(12) United States Patent
Yabuki et al.

(10) Patent No.: US 6,815,207 B2
(45) Date of Patent: Nov. 9, 2004

(54) MOISTURE/WETNESS DETECTING METHOD, MOISTURE/WETNESS DETECTING LABEL, ARTICLES WITH MOISTURE/WETNESS DETECTING FUNCTION, AND DETECTING MATERIAL AND METHOD

(75) Inventors: Yoshiharu Yabuki, Minami Ashigara (JP); Akio Ishizuka, Tokyo (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 09/956,953

(22) Filed: Sep. 21, 2001

(65) Prior Publication Data

US 2002/0061595 A1 May 23, 2002

(30) Foreign Application Priority Data

Sep. 21, 2000 (JP) .................................... P.2000-287118

(51) Int. Cl.[7] ................................................ G01N 7/00
(52) U.S. Cl. ........................ 436/2; 436/39; 422/58; 422/61; 116/311; 73/29.01; 73/73
(58) Field of Search .............................. 422/56, 58, 61; 436/2, 39; 116/200, 211, 227; 73/29.01, 73

(56) References Cited

U.S. PATENT DOCUMENTS

| 4,015,462 | A | * | 4/1977 | Greyson et al. ............. 73/32 R |
| 4,022,211 | A | * | 5/1977 | Timmons et al. ............ 604/361 |
| 5,232,894 | A | * | 8/1993 | Chosa ........................ 503/227 |
| 5,935,745 | A | * | 8/1999 | Ohtsu et al. .................. 430/31 |

FOREIGN PATENT DOCUMENTS

| JP | 61123682 A | * | 6/1986 |
| JP | A2000105230 | | 4/2000 |

* cited by examiner

*Primary Examiner*—Lyle A. Alexander
(74) *Attorney, Agent, or Firm*—Birch, Stewart, Kolasch & Birch, LLP

(57) ABSTRACT

A method of detecting moisture or wetness which enables determination as to whether or not precision instruments or industrial products have undergone improper conditions, is described, which comprises: (i) use of a composite material which contains at least one water-soluble decoloring agent and at least one methine dye whose color disappears upon reaction with the decoloring agent in a state that the decoloring agent and the dye are spatially isolated from each other, and (ii) detection of a history of contact with moisture or water by disappearance of color from the composite material.

14 Claims, 2 Drawing Sheets

MOISTURE/WETNESS DETECTING METHOD, MOISTURE/WETNESS DETECTING LABEL, ARTICLES WITH MOISTURE/WETNESS DETECTING FUNCTION, AND DETECTING MATERIAL AND METHOD

FIELD OF THE INVENTION

The present invention belongs to the technical field of a detecting material and method for judgement as to whether or not easily portable precision equipment for use in the open, such as cameras and mobile communication terminals, has undergone an improper usage condition, e.g., submersion in water or wetting with water, or whether or not articles of the type which are liable to suffer deterioration or have troubles when brought into contact with moisture or water, such as industrial products including precision equipment and drugs, clothing, foodstuffs, various kinds of records and cultural properties, have been in an inappropriate condition, specifically they have been placed under high humidity or have been gotten wet in rain, in the course of transportation or storage.

BACKGROUND OF THE INVENTION

When electronic devices and precision equipment, inclusive of "take-along" cellular phones, which tend to have troubles by rain or water penetration of their interior, cause failures within the term of warranty on products by makers and need repairs, it becomes necessary to determine causes of the failures and judge whether or not the makers should assume responsibility for failures. On the other hand, it is also necessary to judge whether or not articles of the type which are liable to suffer deterioration or have troubles when brought into contact with moisture or water, such as industrial products including precision equipment and drugs, clothing, foodstuffs, various kinds of records and cultural properties, have been in an inappropriate condition, such as a high humidity condition or a condition of exposure to rain, in the course of transportation or storage, and distinguish between responsibility of dealers and that of makers. Such being the cases, it has become necessary to confirm details about exposure to highly humid air or wetting with water, which have happened during transportation, storage or use to become a cause of failure or deterioration, and has been desired to develop a method for simple and accurate detection of exposure to moisture or water.

In JP-A-5-265143 and JP-A-5-232535 (the term "JP-A" as used herein means an "unexamined published Japanese patent application"), substances easily dissolving in water and compounds changing their colors or forms upon contact with water, such as compounds deprived of crystalline water, are disclosed as moisture detecting means. For instance, the substances easily dissolving in water include moisture testing paper made by Toyo Roshi Kaisha, Ltd., Oblate, low molecular weight polyvinyl alcohol and sodium polyacrylate, and the compounds deprived of crystalline water include anhydrous copper sulfate and anhydrous cobalt chloride. However, the use of such means has drawbacks of lacking convenience and being insufficient for clear determination. In addition, JP-A-9-325698 discloses the water-resistant sheet having a water-soluble film window for wet detect, and JP-A-10-2893 discloses the wet-sensing matter printed on a sheet having low water repellency with waterless lithographic printing ink containing a water-soluble dye. In the case of the former detect sheet, wetting is visually perceivable by dissolution of the water-soluble film. In the case of the latter sensing printed matter, on the other hand, wetting is visually perceivable by permeation of the water-soluble dye eluted from printed areas into non-printed areas. However, both cases still have problems with lucidity of standards for determination. Further, JP-A-2000-105230 discloses the wetness detecting method and label using a colorant composition comprising an electron-accepting color-development compound and an electron-donating coloration compound and thereby enabling disappearance of color upon contact with water. However, all the methods cited above hardly permit evaluation of an exposure story under high humidity conditions, which do not yet reach the condition of wetting with water.

SUMMARY OF THE INVENTION

A problem tackled by the invention is to provide a moisture/wetness detecting method which enables judgement as to whether or not easily portable precision equipment intended for use outdoors has undergone an improper usage condition, such as submersion in water or wetting with water, or whether or not articles of the type which are liable to suffer deterioration or have troubles when they are brought into contact with moisture or water have been in an inappropriate condition, specifically they have been placed under high humidity or have been gotten wet in rain, in the course of transportation or storage.

Another problem tackled by the invention is to provide a moisture/wetness detecting label enabling detection of a history of exposure to high humidity or wetting with water by being affixed to the outside or inside of an article which requires detecting whether or not it has undergone exposure to high humidity or wetting with water.

Still another problem tackled by the invention is to provide an article having convenient function for checking on a history of exposure to high humidity or a history of wetting with water by the use of the aforementioned moisture/wetness detecting method or label.

A further problem tackled by the invention is to provide a detecting material that permits easy detection of a history of contact with a liquid like water or a liquid vapor by a change in its color.

A still further problem tackled by the invention is to provide a detecting method that makes it possible to detect easily whether or not various articles have come into contact with a liquid like water or a liquid vapor during use, storage or transportation.

In order to solve the aforementioned problems, the present moisture/wetness detecting method comprises using a composite material which contains at least one water-soluble decoloring agent and at least one methine dye, the color of which disappears upon reaction with the decoloring agent, in a state that the decoloring agent and the dye are spatially isolated from each other, and detecting a history of contact with moisture or water by disappearance of color from the composite material. Further, the present moisture/wetness detecting label enabling solution of the aforementioned problems is characterized in that at least one water-soluble decoloring agent and at least one methine dye, the color of which disappears upon reaction with the decoloring agent, are coated on a support in a state that the decoloring agent and the dye are spatially isolated from each other. Furthermore, the foregoing problems are solved by articles with a moisture/wetness detecting function that are characterized by the provision of a moisture detect component comprising a support coated with at least one water-soluble decoloring agent and at least one methine dye, the color of which disappears upon reaction with the decoloring agent, in a state that the decoloring agent and the dye are spatially isolated from each other.

In addition, the present detecting material that can bring about a solution of the foregoing problems is characterized by comprising at least one decoloring agent and at least one colorant, the color of which disappears upon reaction with the decoloring agent, in a state that decoloring reaction is prevented from proceeding. Therein, the decoloring reaction between part or all of the colorant and the decoloring agent is caused upon contact with the liquid, the liquid vapor or both in which at least either the decoloring agent or the colorant is soluble to result in disappearance of the colorant's color and enables the detection of contacts with the liquid, the liquid vapor or both.

In the present detecting material, the reaction between the colorant and the decoloring agent proceeds upon contact with the liquid, the liquid vapor or both. As a result, part or all of the colorant loses its color, and thereby the contact with liquid, liquid vapor or both is detected. Therefore, the contact of the present detecting material with a liquid, liquid vapor or both can be detected by visually perceivable color change, and evaluation of contact with a liquid, a liquid vapor or both can be made with ease.

In accordance with a preferred embodiment of the present invention, the detecting material comprises a detecting layer comprising at least one layer comprising a decoloring agent and a colorant in a state that the decoloring agent and the colorant are spatially isolated from each other, and at least a part of the detecting layer loses or changes its color upon contact with a liquid, a liquid vapor or both in which at least either the decoloring agent or the colorant is soluble.

In a preferred embodiment of the present detecting material, the detecting layer comprises a decoloring agent layer comprising the decoloring agent as defined above and a colorant layer comprising the colorant as defined above.

In a much preferable embodiment of the present detecting material, the decoloring agent and colorant layers comprise a binder capable of absorbing the liquid, the liquid vapor or both as defined above.

When the liquid is water, gelatin is preferred as the binder.

In a further preferred embodiment of the present detecting material, the material further comprises a member for leaving a space between the decoloring agent layer and the colorant layer in a state that the liquid, the liquid vapor or both is capable of permeating through the member.

In another preferable embodiment of the present detecting material, the material further comprises an interlayer that is sandwiched between the decoloring agent layer and the colorant layer and has channels leading to both the decoloring agent layer and the colorant layer.

Therein, it is preferable that the interlayer have a thickness of 0.1 to 100 $\mu$m.

In still another preferable embodiment of the present detecting material, the material further comprises underneath or inside the detecting layer a display plane bearing characters, drawings or both, and thereby the characters, drawings or both can be visually recognized when a part or all of the detecting layer loses its color.

In the present detecting materials according to the foregoing embodiments, it is preferable that the colorant be a methine dye or an azomethine dye.

In order to solve the aforementioned problems, the present method for detecting at least one of a storage history, a use history and a transportation history of an article comprises fitting an article with a detecting material according to the invention, and checking after at least one of storage, use and transportation of the article whether or not the detecting material has lost its color.

BRIEF DESCRIPTION OF DRAWINGS

FIG. 1A is a cross-sectional diagram of the detecting label, FIG. 1B is an oblique view of the detecting label before use, and FIG. 1C is an oblique view of the detecting label after use.

FIG. 2A is a cross-sectional diagram of the detecting label, FIG. 2B is an oblique view of the detecting label before use, and FIG. 2C is an oblique view of the detecting label after use.

Figure 1A:
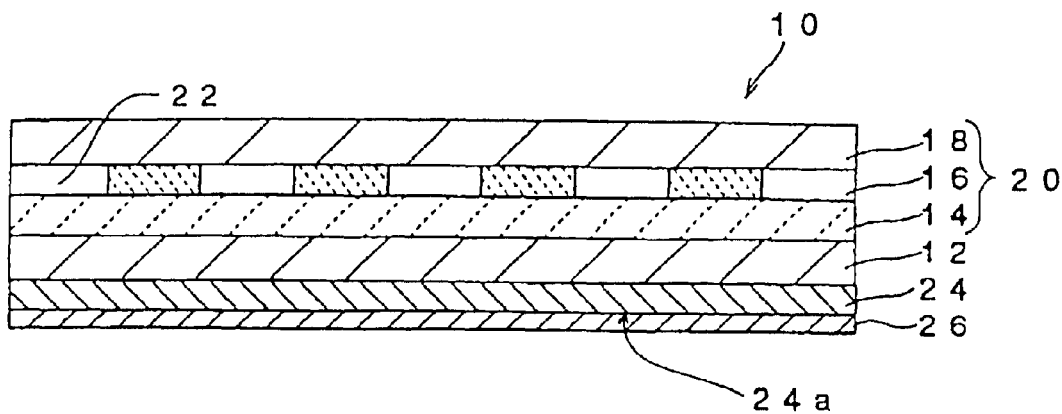
FIGS. 1A, 1B and 1C show schematic illustrations of a detecting label relating to one embodiment of the invention. Herein.

The reference numerals and marks in the figures stand for the following members, respectively:

| | |
|---|---|
| 10, 10' | Detecting label |
| 12, 12' | Support |
| 12'a | Display plane |
| 14 | Decoloring agent layer |
| 16 | Interlayer |
| 18 | Colorant layer |
| 20 | Detecting layer |
| 22 | Channel |
| 24 | Adhesion layer |
| 24a | Adhesive face |
| 26 | Release paper |

DETAILED DESCRIPTION OF THE INVENTION

The present invention is described below in detail.

Colorants used in the invention may be any of colorants in so far as they can lose or change their colors upon contact with decoloring agents as described below. Of colorants, methine dyes, azomethine dyes and azo dyes are preferred over the others. In particular, methine dyes or azomethine dyes are preferably used. When the invention is applied to moisture and/or wetness detection, colorants used are preferably methine dyes, especially water-soluble methine dyes.

In the case of using methine dyes as colorant, decoloring agents used in the invention may be any of decoloring agents in so far as they can decolor the methine dyes. Examples of such decoloring agents include nucleophilic reagents (e.g., compounds providing sulfite ions or hydroxyl ions, primary or secondary amines such as hydroxylamine, methylamine and dimethylamine, guanidine and amidine), oxidants (e.g., sodium perborate, ammonium persulfate), and reducing agents (e.g., sodium hydrosulfite). Of these decoloring agents, compounds providing sulfite or hydroxyl ions and hydroxylamine are preferred over the others. In particular, compounds providing sulfite ions are preferably used. When the invention is applied to moisture and/or wetness detection, it is preferable to use water-soluble compounds as decoloring agent.

Methine dyes preferably used in the invention as colorants capable of causing disappearance of their colors are compounds represented by the following formula (I), (II), (III), (IV) or (V).

| | | |
|---|---|---|
| Oxonol dyes | Ak = Lo - Ae | (I) |
| Cyanine dyes | Bs = Lo - Bo | (II) |
| Meracyanine dyes | Bs = Le = Ak | (III) |
| Arylidene dyes | Ak = Lo - Ar | (IV) |
| Styryl dyes | Bo - Le - Ar | (V) |

In the above formulae, Ak represents a keto-form acidic nucleus, Ae represents an enol-form acidic nucleus, Bs represents a basic nucleus, Bo represents an onium body of basic nucleus, Ar represents an aromatic carbon ring or an aromatic hetero ring, Lo represents a methine chain constituted of an odd number of methine groups, and Le represents a methine chain constituted of an even number of methine groups. Further, it is preferable that each of the compounds of formula (I), (II), (III), (IV) or (V) has a group or groups capable of imparting water solubility per one molecule (such as sulfo group, phosphono group, carboxyl group, sulfonamido group, arylsulfamoyl group, sulfonylcarbamoyl group, carbonylsulfamoyl group, enol group of oxonol dye or phenolic hydroxyl group).

When the groups imparting water solubility to dyes are groups providing water solubility in a neutral sate, such as sulfo and phosphono groups, the dyes can be used as water-soluble dyes in the form of water solution. On the other hand, in the case of groups capable of providing water solubility only when the pH is increased beyond neutral, such as carboxyl group, sulfonamido group, arylsulfamoyl group, sulfonylcarbamoyl group, carbonyl-sulfamoyl group, enol group of oxonol dye or phenolic hydroxyl group, the dyes having such groups can be used in the form of a dispersion of fine solid particles. Using the dyes as a dispersion of fine solid particles is advantageous in that the reactivity with moisture can be arbitrarily controlled, so the sensitivity to moisture can be adjusted, and the dyes can have improved storability.

As an acidic nucleus represented by Ak or Ae, a cyclic ketomethylene compound or a compound having a methylene group sandwiched between electron-attracting groups is preferable. Examples of a cyclic ketomethylene compound as the acidic nucleus include 2-pyrazoline-5-one, rhodanine, hydantoin, thiohydantoin, 2,4-oxazolidinedione, isooxazolone, barbituric acid, thiobarbituric acid, indanedione, dioxopyrazolopyridine, hydroxypyridine, pyrazolidinedione, 2,5-dihydrofuran-2-one and pyrroline-2-one. Of these compounds, 2-pyrazoline-5-one, isooxazolone, barbituric acid and dioxopyrazolopyridine and hydroxypyridine are preferred over the others. Those acidic nuclei may have substituent groups. And it is preferable that such an acidic nucleus be bound to a methine group at the site of a carbon atom therein.

The compound having a methylene group sandwiched between electron-attracting groups can be represented by $Z^1CH_2Z^2$, wherein $Z^1$ and $Z^2$ are independent of each other, and they each represents —CN, —$SO_2R^1$, —$COR^1$, —$COOR^2$, —$CONHR^2$, —$SO_2NHR^2$, —$C[=C(CN)_2]R^1$ or —$C[=C(CN)_2]NHR^1$. $R^1$ represents an alkyl group, an aryl group or a heterocyclic group, and $R^2$ represents a hydrogen atom, an alkyl group, an aryl group or a heterocyclic group. These groups each may have a substituent group.

Examples of a basic nucleus represented by Be include pyridine, quinoline, indolenine, oxazole, imidazole, thiazole, benzoxazole, benzimidazole, benzothiazole, oxazoline, naphthoxazole and pyrrole. These nuclei each may have a substituent group. And it is preferable that the binding site of such a basic nucleus to a methine group be present on a carbon atom.

Examples of an aromatic carbon ring represented by Ar include a phenyl group and a naphthyl group, which each may have a substituent group. In particular, phenyl groups substituted with a dialkylamino group, a hydroxyl group and an alkoxy group respectively are preferred over the others. Examples of a hetero ring, from which an aromatic heterocyclic group represented by Ar is derived by removal of one hydrogen atom, include pyrrole, indole, furan, thiophene, imidazole, pyrazole, indolizine, quinoline, carbazole, phenothiazine, phenoxazine, indoline, thiazole, pyridine, pyridazine, thiadiazine, pyran, thiopyran, oxadiazole, benzoquinoline, thiadiazole, pyrrolothiazole, pyrrolopyridazine, tetrazole, oxazole, coumarin and cumarone. These rings each may have a substituent group. And it is preferable that the binding site of such an aromatic heterocyclic group to a methine group be present on a carbon atom.

Methine groups represented by Lo and Le respectively may have substituent groups, and these substituent groups may combine with each other to complete a 5- or 6-membered ring (e.g., cyclopentene, cyclohexene).

There are no particular restrictions as to substituent groups the above-described groups may have, but suitable examples thereof include a sulfo group, a phosphono group, a carboxyl group, 1–10C sulfonamido groups (such as methanesulfonamido, benzenesulfonamido, butanesulfonamido and n-octanesulfonamido), 0–10C sulfamoyl groups (such as unsubstituted sulfamoyl, methylsulfamoyl, phenylsulfamoyl and butylsulfamoyl), 2–10C sulfonylcarbamoyl groups (such as methanesulfonylcarbamoyl, propanesulfonylcarbamoyl and benzenesulfonylcarbamoyl), 1–10C acylsulfamoyl groups (such as acetylsulfamoyl, propionylsulfamoyl, pivaloylsulfamoyl and benzoylsulfamoyl), 1–8C chain or cyclic alkyl groups (such as methyl, ethyl, isopropyl, butyl, hexyl, cyclopropyl, cyclohexyl, 2-hydroxyethyl, 4-carboxylbutyl, 2-methoxyethyl, benzyl, phenetyl, 4-carboxybenzyl and 2-diethylaminoethyl), 2–8C alkenyl groups (such as vinyl and allyl), 1–8C alkoxy groups (such as methoxy, ethoxy and butoxy), halogen atoms (such as F, Cl and Br), 0–10C amino groups (such as unsubstituted amino, dimethylamino, diethylamino and carboxyethylamino), 2–10C ester groups (such as methoxycarbonyl), 1–10C amido groups (such as acetamido and benzamido), 1–10C carbamoyl groups (such as unsubstituted carbamoyl, methylcarbamoyl and ethylcarbamoyl), 6–10C aryl groups (such as phenyl, naphthyl, 4-carboxyphenyl, 3-carboxyphenyl, 3,5-dicarboxyphenyl, 4-methanesulfonamido-phenyl and 4-butanesulfonamidophenyl), 6–10C aryloxy groups (such as phenoxy, 4-carboxyphenoxy, 3-methylphenoxy and naphthoxy), 1–8C alkylthio groups (such as methylthio, ethylthio and octylthio), 6–10C arylthio groups (such as phenylthio and naphthylthio), 1–10C acyl groups (such as acetyl, benzoyl and propanoyl), 1–10C sulfonyl groups (such as methanesulfonyl and benzenesulfonyl), 1–10C ureido groups (such as ureido and methylureido), 2–10C urethane groups (such as methoxycarbonylamino and ethoxycarbonylamino), a cyano group, a hydroxyl group, a nitro group, and heterocyclic groups (such as 5-carboxybenzoxazolyl, pyridyl, sulfolanyl, furanyl, pyrrolyl, pyrrolidinyl, morpholinyl, morpholino, piprerazinyl and pyrimidinyl).

Of the dyes of formula (I), (II), (III), (IV) or (V), those represented by formula (I), (IV) or (V) are preferred over the others. And those represented by formula (I) or (IV) are preferable to those represented by formula (V). In particular, the dyes of formula (I) are preferably used.

Examples of compounds represented by formula (I), (II), (III), (IV) or (V) which can be used in the invention are illustrated below, but it should be understood that these examples are not to be construed as limiting the scope of the invention in any way.

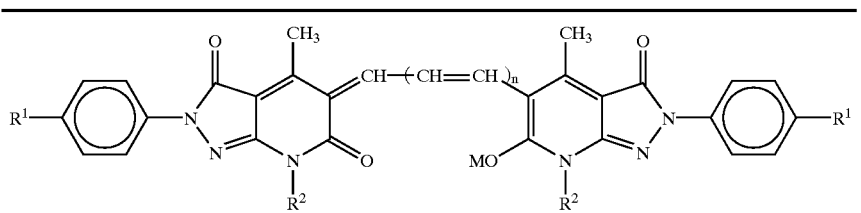

|    | R¹       | R²                | M  | n |
|----|----------|-------------------|----|---|
| 1  | SO₃K     | H                 | H  | 1 |
| 2  | SO₃Na    | H                 | H  | 2 |
| 3  | —CO₂Na   | H                 | Na | 1 |
| 4  | —CO₂H    | H                 | H  | 1 |
| 5  | —SO₃K    | —C₆H₄—SO₃K        | K  | 1 |
| 6  | —SO₃K    | —CH₂CH₂SO₃K       | K  | 1 |
| 7  | —CO₂H    | —C₆H₄—CO₂H        | H  | 1 |
| 8  | —CO₂H    | —C₆H₄—CO₂H        | H  | 2 |
| 9  | —SO₃Na   | —CH₂CO₂Na         | Na | 1 |
| 10 | —SO₃K    | —CH₂CH₂OH         | K  | 1 |

|    | R¹      | R²                 | R³    | L                              | M  |
|----|---------|--------------------|-------|--------------------------------|----|
| 11 | CN      | —C₆H₄—SO₃K         | CH₃   | =CH—(CH=CH)₂—                  | K  |
| 12 | CN      | —CH₂CH₂SO₃Na       | CH₃   | =CH—CH=CH—                     | Na |
| 13 | —CONH₂  | —CH₂CH₂SO₃Na       | CH₃   | =CH—CH=CH—                     | Na |
| 14 | —CONH₂  | —CH₂CO₂K           | CH₃   | =CH—CH=CH—                     | K  |
| 15 | —CN     | 2-methyl-1,4-di(SO₃K)phenyl | CH₃ | =CH—CH=C(CH₃)—CH=CH— | K  |
| 16 | —CN     | —CH₂CH₂SO₃K        | —CO₂K | =CH—CH=CH—                     | K  |
| 17 | H       | —C₆H₄—SO₃Na        | CH₃   | =CH—CH=C(N-pyrrolidin-2-one)—CH=CH— | Na |

-continued
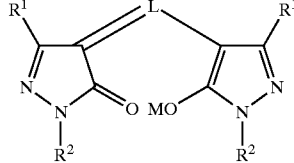
| | R¹ | R² | L | M |
|---|---|---|---|---|
| 18 | CN | 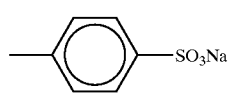 4-SO₃Na-phenyl | =CH—CH=CH—CH=CH— | Na |
| 19 | CN | 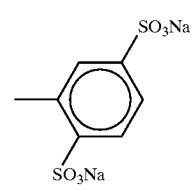 3,5-bis(SO₃Na)-phenyl | =CH—CH=C(CH₃)—CH=CH— | Na |
| 20 | CN | 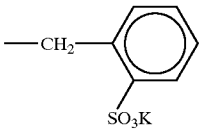 —CH₂-(2-SO₃K-phenyl) | =CH—CH=CH— | K |
| 21 | CN | —CH₂CH₂SO₃K | =CH—CH=CH— | K |
| 22 | —CO₂C₂H₅ | 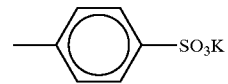 4-SO₃K-phenyl | =CH—CH=CH— | H |
| 23 | —CO₂C₂H₅ | 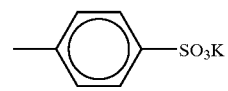 4-SO₃K-phenyl | =CH— | H |
| 24 | —CO₂H | 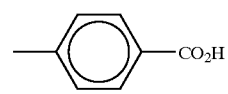 4-CO₂H-phenyl | =CH—(CH=CH)₂— | H |
| 25 | —CO₂C₂H₅ | 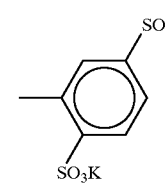 3,5-bis(SO₃K)-phenyl | =CH—(CH=CH)₂— | H |
| 26 | —COCH₃ | 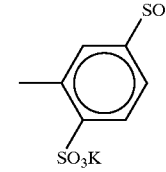 3,5-bis(SO₃K)-phenyl | =CH—(CH=CH)₂— | H |
| 27 | —CONHCH₃ | 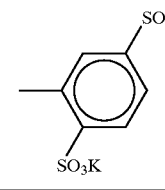 3,5-bis(SO₃K)-phenyl | 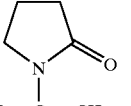 =CH—CH=C(N-pyrrolidinonyl)—CH=CH— | H |

-continued

[Structure: bis-isoxazolone with R groups, L linker, and MO/O substituents]

| | R | L | M |
|---|---|---|---|
| 28 | 4-methylphenyl-SO₃K (*p*-tolyl-SO₃K) | =CH—CH=CH—CH=CH— | H |
| 29 | 4-methylphenyl-NH-CO-(3-SO₃K-phenyl) | =CH—CH=CH— | K |
| 30 | 3-methylphenyl-NH-CO-(2-SO₃Na-phenyl) | =CH—CH=CH— | Na |
| 31 | n-C₄H₉ | =CH—CH=CH—CH=CH— | H |

[Structure: bis-barbituric acid type with R¹, R² groups and L linker]

| | R¹ | R² | L | M |
|---|---|---|---|---|
| 32 | H | 4-CO₂H-phenyl | =CH—(CH=CH)₂— | H |
| 33 | H | 4-OH-phenyl | =CH—(CH=CH)₂— | H |
| 34 | H | 4-SO₃K-phenyl | =CH—CH=CH— | H |
| 35 | H | 4-SO₃K-phenyl | =CH—CH=C(CONH₂)—CH=CH— | H |
| 36 | CH₂CH₂SO₃Na | CH₂CH₂SO₃Na | =CH—CH=CH— | H |
| 37 | —CH₃ | CH₂CH₂SO₃Na | =CH—CH=CH—CH=CH— | Na |

[Structure: pyrazolone with R¹, R², Ar and n]

| | R¹ | R² | Ar | n |
|---|---|---|---|---|

-continued
| | | | | |
|---|---|---|---|---|
| 38 | CN | 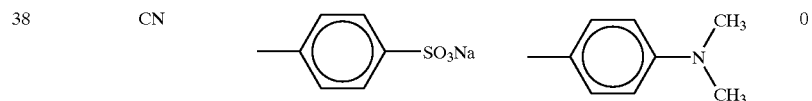 | | 0 |
| 39 | CN | 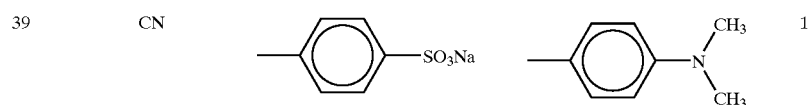 | | 1 |
| 40 | —CON⟨morpholine⟩ | 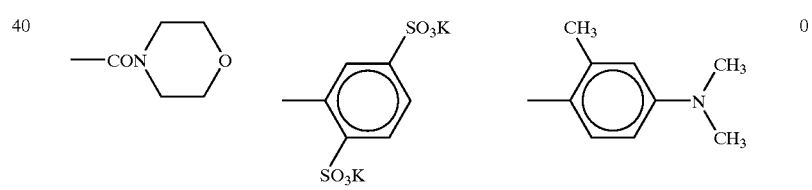 | | 0 |
| 41 | —CO$_2$C$_2$H$_5$ | 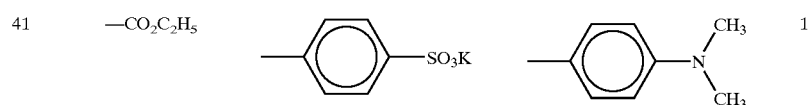 | | 1 |
| 42 | CN | 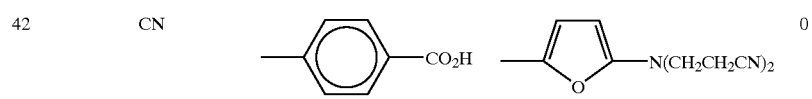 | | 0 |
| 43 | CH$_3$ | 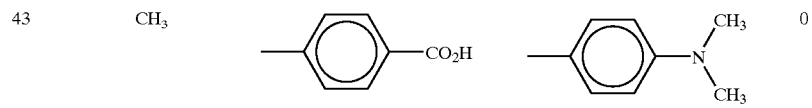 | | 0 |
| 44 | —CO$_2$C$_2$H$_5$ | 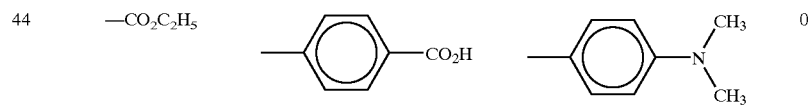 | | 0 |
| 45 | CH$_3$ | 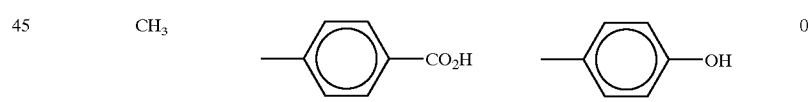 | | 0 |
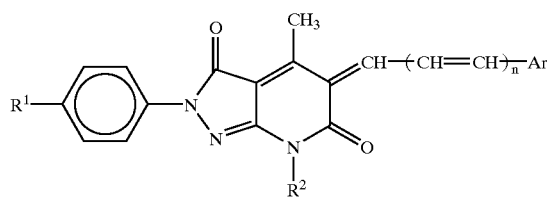
| | R$^1$ | R$^2$ | Ar | n |
|---|---|---|---|---|
| 46 | —CO$_2$H | 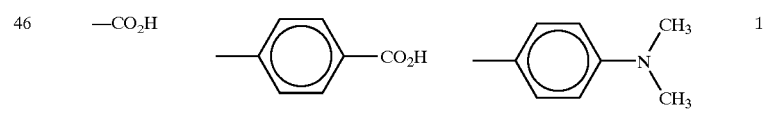 | | 1 |
| 47 | —CO$_2$H | 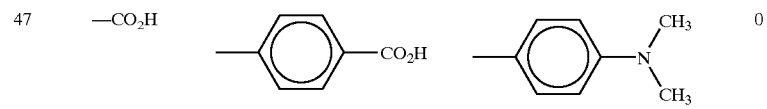 | | 0 |

-continued
| | | | | |
|---|---|---|---|---|
| 48 | —CO₂H | H | 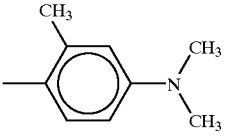 | 0 |
| 49 | —CO₂H | H | 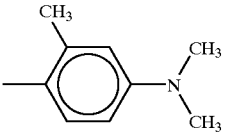 | 1 |
| 50 | —CO₂H | H |  | 0 |
| 51 | —CO₂H | H | 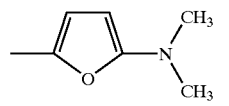 | 0 |
| 52 | —CO₂H | H | 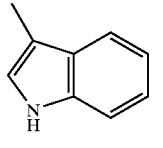 | 0 |
53
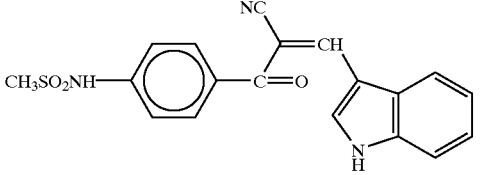
54
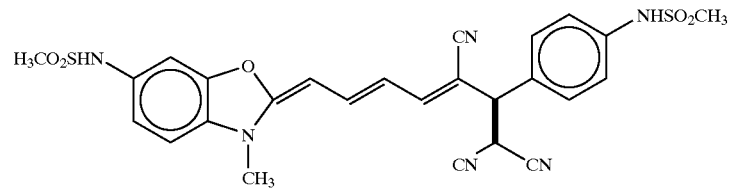
55
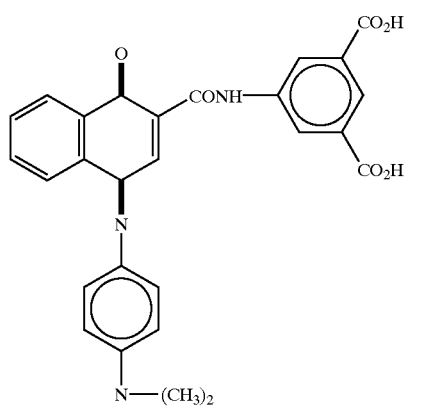

-continued

56 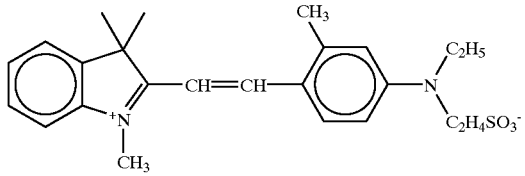

57 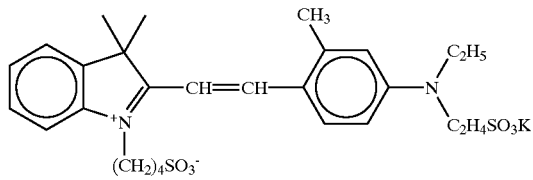

58 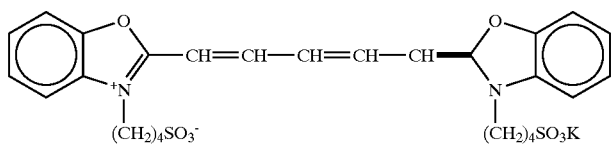

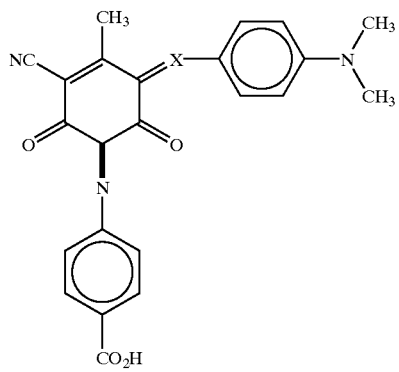

59          X=CH
60          X=N

Dyes capable of causing disappearance of their colors, which can be used in the invention, can be synthesized using or according to the methods as described in F. M. Harmer, *Heterocyclic Compounds—Cyanine Dyes and Related Compounds*, John Wiley and Sons, New York, London (1964), JP-A-6-313939 and WO88/04794.

The foregoing dye compounds represented by formula (I), (II), (III), (IV) or (V) can be introduced into a colorant layer relating to the invention by various methods as described below.

For instance, a method of directly dispersing a dye compound can be used.

In another usable method, a dye compound is added in the form of a solution prepared by dissolving the compound in an appropriate solvent (e.g., water, methanol, ethanol, propanol, the halogenated alcohol as disclosed in JP-A-48-9715 and U.S. Pat. No. 3,756,830, acetone, N,N-dimethylformamide, pyridine or a mixture of two or more of these solvents) . Of the solvents described above, water, methanol and a water-methanol mixture are preferably used.

On the other hand, the dye compounds represented by formula (I), (II), (III), (IV) or (V) may be used as dispersions of solid fine particles (microcrystalline). By using the dyes in the form of solid dispersions, diffusion of the dyes can be inhibited, and so bleeding can be reduced. As a result, a sign of wetting history becomes clear and the determination by visual observation can be easily made. The solid fine particle (microcrystalline) dispersion of a dye can be prepared mechanically using a known method of milling finely (with a ball mill, a vibrating ball mill, a planetary ball mill, a sand mill, a colloid mill, a jet mill or a roller mill) in the presence of a dispersant and, if desired, an appropriate solvent (such as water or alcohol). In addition, fine (crystalline) particles of a dye can also be obtained by using a method of dissolving the dye in an appropriate solvent in the presence of a dispersant and then adding the resulting solution to a poor solvent for the dye to form a microcrystalline precipitate, or a method of dissolving the dye by pH control and then changing the pH to form a microcrystalline precipitate. The thus obtained fine (crystalline) particles of a dye are dispersed into an appropriate binder, and can be made into an almost uniform solid particle dispersion. Descriptions of specific methods usable therein can be found in JP-A-56-12639, JP-A-55-155350, JP-A-55-155351, JP-A-63-27838, JP-A-63-197943 and European Patent 15602. Further, fine-particle metal salts to which dyes are adsorbed may be utilized. Descriptions about such cases can be found in U.S. Pat. Nos. 2,719,088, 2,496,841 and 2,496, 843, and JP-A-60-45237.

Each of the dyes of formula (I), (II), (III), (IV) or (V) can be used in any amount in so far as it is perceivable by eyes, but it is preferable that the optical density reached by using the dye be within the range of 0.5 to 3.0. Specifically, it is preferable to add each dye in an amount of 0.5 to 1000 mg/m$^2$, more preferably 1 to 500 mg/m$^2$, particularly preferably 5 to 200 mg/m$^2$.

Examples of a binder which can carry the foregoing decoloring agents and methine dyes include hydrophilic polymeric binders (such as polyvinyl alcohol, polyethylene glycol, cellulose and derivatives thereof, alginic acid and salts thereof, carboxyvinyl polymers, polyethylene oxide, sodium polyacrylate, polyvinyl pyrrolidone, gelatin, gum arabic, carrageenan, agar, pectin and starch.) Of these binders, gelatin and polyvinyl alcohol, especially gelatin, are preferred over the others.

Further, additives may be added in the invention for the purpose of fixing dyes, enhancing decoloring capability, elevating dispersibility and improving storabilities of colorants and decolored compounds.

Furthermore, additives may be added with the invention of heightening storability of decoloring agent (nucleophilic agent). Examples of additives usable in the invention include surfactants, discoloration inhibitors for inhibiting dyes from discoloring, ultraviolet agents, hardeners for hygroscopicity control of hydrophilic binders, and preservatives. As these additives, those hitherto used for silver halide photographic materials are suitable. Specifically, descriptions of preferable additives can be found in JP-A-62-215272 and Research Disclosure, vol. 176 (1978, XI), D-17843. In addition to those additives, it is also possible to use mordants for inhibiting dyes from diffusing to prevent bleeding and render visual recognition easier in the detection (preferable examples of which can be found in U.S. Pat. Nos. 2,548,564, 4,124,386 and 3,625,694), and decoloring agent (nucleophilic agent) storage stabilizers for improving a shelf life of detecting label (e.g., reducing agents, such as ascorbic acid in the case of using sulfite ion as decoloring agent).

In the case of a detecting label as one embodiment of the invention, dyes incapable of disappearance of their colors may be used in combination with the dyes capable of disappearance of their colors. By the combined use of such dyes, a contrast between different colors can be provided between color retention areas and areas having undergone color disappearance reaction to make visual recognition easier, compared with a contrast between white and color brought by the independent use of dyes capable of disappearance of their colors.

The present moisture/wetness detecting label can be made up by coating on a support a decoloring agent and a dye capable of disappearance of its color together with their respective binders in separate layers so as to spatially isolate the decoloring agent from the dye. Diffusion of the dye and/or the decoloring agent is caused by the action of moisture or water, and the dye-to-decoloring agent contact occurs. As a result, the color of the dye disappears to effect detection of moisture or water. Between these two layers, a hydrophilic interlayer for time control of diffusion may be present, or a hydrophobic isolation wall for partial control of diffusion may be present. Utilization of the hydrophobic isolation wall for partial control of diffusion, or partial control of color disappearance, enables ON-OFF control of diffusion to effect appearance of letters or marks and to make the determination easier.

The present detecting material is characterized in that at least one decoloring agent and at least one colorant losing its color upon reaction with the decoloring agent are contained in a state that the decoloring reaction does not proceed, and color disappearance occurs when the material is brought into contact with a liquid and/or liquid vapor in which at least either the decoloring agent or the colorant has solubility and causes reaction between the decoloring agent and part or all of the colorant. Herein, the expression "state that the decoloring reaction does not proceed" is intended to include not only a state that the reaction does not proceed by spatial isolation of the colorant from the decoloring agent but also a state that the colorant and the decoloring agent are in a contact state but reaction between them does not proceed because of high activation energy for the reaction. In the present detecting material, reaction between the decoloring agent and the colorant takes place upon contact with a liquid and/or liquid vapor in which at least either the colorant or the decoloring agent shows solubility. In one mode of containing the colorant and the decoloring agent in a spatially isolated state, contact with the foregoing liquid and/or liquid vapor causes diffusion of the colorant and/or the decoloring agent and releases the colorant and the decoloring agent from the isolated state, resulting in progress of the decoloring reaction. In the other mode of containing the colorant and the decoloring agent in a contact state, the colorant and/or the decoloring agent causes dissolution upon contact with the foregoing liquid and/or liquid vapor, and thereby the activation energy for decoloring reaction is lowered and the reaction proceeds. In the present detecting material, the contact with a liquid and/or liquid vapor (simply described as "liquid or the like" hereinafter, too) is detected by color disappearance. As to modes of detecting contact with a liquid or the like, the present detecting material includes a mode of detecting the contact by overall disappearance of its color, a mode of detecting the contact by appearance of letters or patterns through partial disappearance of its color, and a mode of detecting the contact by baring a display plane, on which letters or patterns are drawn, through disappearance of its color.

Examples of a mode of incorporating a colorant and a decoloring agent in a spatially isolated state include a mode of incorporating the colorant and the decoloring agent into separate layers, a mode of incorporating one of those components inside capsules and the other outside the capsules, a mode of incorporating those components into separate capsules, and a mode of incorporating those components independently into phases in a state of phase separation (e.g., dispersing those components independently as different solid particles, or incorporating one component as solid particles in one phase and the other component as solid particles in the other phase). The isolated state in which the colorant and the decoloring agent are kept can be released by contact with the foregoing liquid and/or liquid vapor. For instance, penetration of the liquid and/or liquid vapor into a space isolating the colorant from the decoloring agent, or absorption of the liquid and/or liquid vapor by a member holding the colorant and the decoloring agent in an isolated state (e.g., a binder in each layer, or microcapsule walls) enables diffusion of both or either of the colorant and the decoloring agent into the liquid or the member having absorbed the liquid, and thereby the colorant and the decoloring agent are brought into contact with each other to result in disappearance of the color from the colorant. In another mode, the colorant in a solid state and/or the decoloring agent in a solid state dissolves or deliquesces by absorbing the liquid and/or liquid vapor, and both colorant and decoloring agent or either of them diffuses to come into contact with each other; as a result, the color of the colorant disappears.

As one mode for carrying out the present invention, mention may be made of a detecting label comprising a detecting layer comprising at least one layer containing the decoloring agent and the colorant in a spatially isolated state. In the detecting label, at least part of the detecting layer loses or changes its color upon contact with a liquid and/or liquid vapor in which at least either the decoloring agent or the colorant has solubility, and thereby the contact with the liquid is detected. The detecting layer can be structured to comprise a decoloring agent layer containing a decoloring agent as described above and a colorant layer containing a colorant as described above. On the other hand, the detecting layer may be constituted of a single layer containing the colorant inside microcapsules and the decoloring agent outside the microcapsules. The detecting label may adopt a mode of detection in which contact with the liquid and/or liquid vapor is detected by disappearance of color from the detecting layer, or a mode of detection in which the contact is detected by change in color of the detecting layer. For instance, it is possible to constitute the detecting layer such that the decoloring agent layer is colored with a dye of the type which does not lose its color. Therein, the color of the detecting layer before contact with the liquid and/or liquid vapor is a mixture of the colorant's color and the dye's color, but after the contact the color of the detecting layer is changed to the color of the dye because the color of the colorant disappears.

In the mode of forming the colorant layer and the decoloring agent layer, the isolated state can be released by incorporating binders capable of absorbing the liquid and/or liquid vapor into the colorant layer and the decoloring agent layer and enhancing the diffusibilities of the colorant and the decoloring agent through absorption of the liquid and/or liquid vapor by the binders. When the liquid is water, hydrophilic binders are used as the binders. In particular, gelatin is preferably used.

When the decoloring agent layer and the colorant layer are in contact with each other in the detecting label having the decoloring agent layer and the colorant layer, and decoloring reaction proceeds due to gradual diffusion of the colorant and the decoloring agent even under circumstances free of liquid to be detected, it is preferable for the detecting label to be equipped with a member for leaving a space between the colorant layer and the decoloring agent layer. This separation member separates the decoloring agent layer from the colorant layer in a state that the liquid, the liquid vapor or both can permeate a space between the colorant layer and the decoloring agent layer. This separation member can be structured to be an interlayer sandwiched between the decoloring agent layer and the colorant layer. For instance, by arranging an interlayer having channels leading to both the decoloring agent layer and the colorant layer in such a manner that the interlayer is sandwiched between the colorant layer and the decoloring agent layer, the decoloring agent layer can be separated from the colorant layer, and besides, the liquid and/or liquid vapor penetrates the channels, thereby enabling diffusion contact between the colorant and the decoloring agent. It is preferable that the interlayer having channels be made up of a material of the kind which absorb neither the liquid nor the liquid vapor. When the liquid is water, the interlayer is preferably made up of a hydrophobic material. On the other hand, a film having no channels but enabling diffusion of the liquid may be arranged as the interlayer sandwiched between the decoloring agent layer and the colorant layer. The material properties and thickness of the interlayer, and the diameter of channels (or the aperture area rate) are important in controlling the progression speed and the critical humidity of the decoloring reaction, and those factors can be designed and selected appropriately depending on the desired purposes.

Further, embodiments of the present detecting material are illustrated using drawings.

Figure 1B:
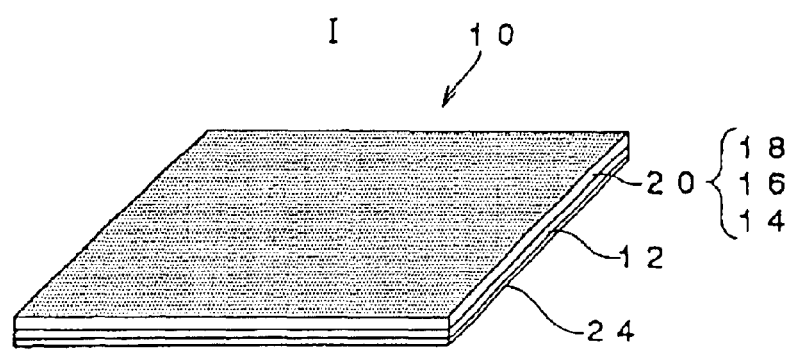
Figure 1C:
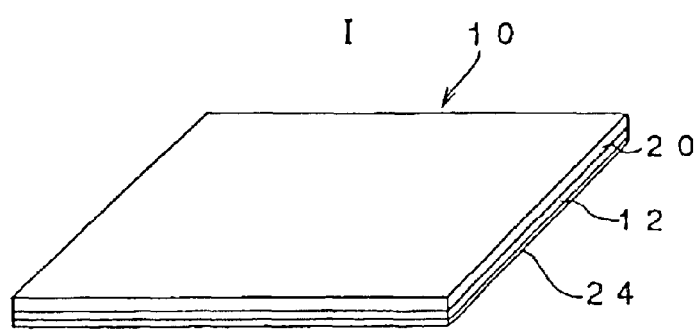

FIG. 1A shows a schematic sectional diagram of a detecting label relating to a mode for carrying out the invention, FIG. 1B shows an oblique view of the detecting label before contact with water, and FIG. 1C is an oblique view of the detecting label after contact with water.

The detecting label 10 is structured to have a detecting layer 20 on a white support 12. The detecting layer 20 is constituted of a decoloring agent layer 14 comprising a water-soluble decoloring agent and a hydrophilic binder, such as gelatin, a colorant layer 18 comprising a colorant, such as a methine dye, and a hydrophilic binder such as gelatin, and an interlayer 16 sandwiched between the decoloring agent layer 14 and the colorant layer 18. Inside the interlayer 16, a plurality of fine channels 22 are formed. On the back of the support 12, an adhesion layer 24 containing an adhesive is formed. This adhesion layer permits sticking the detecting label on an article. Before use, a release paper 26 is affixed to the adhesive face 24a. And the release paper 26 is peeled apart at the time of use, and the label is affixed to an article.

Before the detecting label is brought into contact with water or moisture, as shown in FIG. 1B, the interlayer 16 keeps the decoloring agent layer 14 and the colorant layer 18 in a non-contact state, and decoloring reaction does not proceed between the decoloring agent and the colorant. Accordingly, the color of the colorant layer 18 is perceptible when viewed from outside I. When the detecting label 10 is exposed to water or moisture, the hydrophilic binders in the colorant layer 18 and the decoloring agent layer 14 absorb the water or the moisture and, at the same time, the channels 22 are also permeated with the water and the moisture. The colorant layer 18 and the decoloring agent layer 14 swell with the absorbed water or moisture and channels 22 also swells. As a result, they come into contact with each other. More specifically, the colorant held in the colorant layer 18 and/or the decoloring agent held in the decoloring agent layer 14 diffuses through the water-absorbed layer, and further reaches the other layer via the water permeating through channels 22 (or the hydrophilic binder impregnated with water) and comes into contact with each other. As a result, the decoloring reaction proceeds. In this case, as shown in FIG. 1C, the color of the colorant layer 18 disappears and the white color of the support 12 is seen when viewed from outside I. By this change in color of the detecting layer 20 from the color of the colorant to the white color of the support 12, the contact of the detecting label 10-affixed article with water or moisture can be detected.

It is preferable for the hydrophilic binders contained in the decoloring agent layer 14 and the colorant layer 18 to have water- or moisture-absorbing properties. Such hydrophilic binders include the same hydrophilic polymers as described above, but polyvinyl alcohol and gelatin are preferred over the others. In particular, gelatin is preferably used. The thickness of the decoloring agent layer 14 and that of the colorant layer 18 affect the sensitivity of the detecting label, so they are adjusted depending on the intended purpose of the detecting label. When the detecting label is used for detecting not only water but also moisture, it is generally preferable for the decoloring agent layer 14 and the colorant layer 18 each to have a thickness of 0.1 to 50 $\mu$m, more preferably 0.5 to 20 $\mu$m.

It is preferable that the content of decoloring agent in the decoloring agent layer 14 be in excess of the content of the colorant in the colorant layer 18. Specifically, the amount of decoloring agent used is preferably from 1.0 to 20 equivalents based on the amount of the colorant. When the detecting label is used for detecting not only water but also moisture, the colorants preferably used therein are methine dyes. In particular, methine dyes represented by the foregoing formula (I), (II), (III), (IV) or (V) can be preferably used. The decoloring agent contained in the decoloring agent layer 14 is preferably a water-soluble compound, particularly preferably a water-soluble compound capable of providing sulfite ion.

The interlayer 16 keeps the decoloring agent layer 14 and the colorant layer 18 separated, and besides, it has channels 22 enabling contact between the decoloring agent in the decoloring agent layer 14 and the colorant in the colorant layer 18 when the detecting label is brought into contact with water or moisture. For fully achieving such a function, it is preferable for the interlayer 16 to have a thickness of 0.1 to 100 μm, more preferably 5 to 50 μm. The aperture area rate of the interlayer 16 is generally from 5 to 95%, preferably 15 to 85%. Further, it is preferable for the interlayer 16 to contain an adhesive for bonding to the decoloring agent layer 14 and the colorant layer 18. Furthermore, it is preferable that the interlayer 16 be hydrophobic so as to inhibit the colorant in the colorant layer 18 from undergoing decoloring reaction when the detecting label is not in contact with water or moisture. As a main component of the adhesive, rubber polymer (e.g., styrene-butadiene copolymer, polyisobutylene), acrylic polymer, polyvinyl alcohol or polyvinyl ether can be used. To such a main component are generally added an adhesion imparting agent (e.g., rosin, rosin ester, ester gum, cumarone resin, cumarone-indene resin, terpene resin, hydrocarbon resin, oil-soluble phenol resin), a softening agent (e.g., fatty acid ester, animal and vegetable oils and fats, waxes and heavy components of petroleum), and a pigment (e.g., zinc white). Further, a filler, an aging inhibitor and a stabilizer may be added, if desired.

The interlayer 16 having channels 22 can be made by forming a uniform layer containing an adhesive and other additives and then partially boring through holes in the layer. On the other hand, the interlayer may be formed using a printing technique, wherein a pattern perforated with holes for channels is printed with a tacky solution containing an adhesive.

Figure 2A:
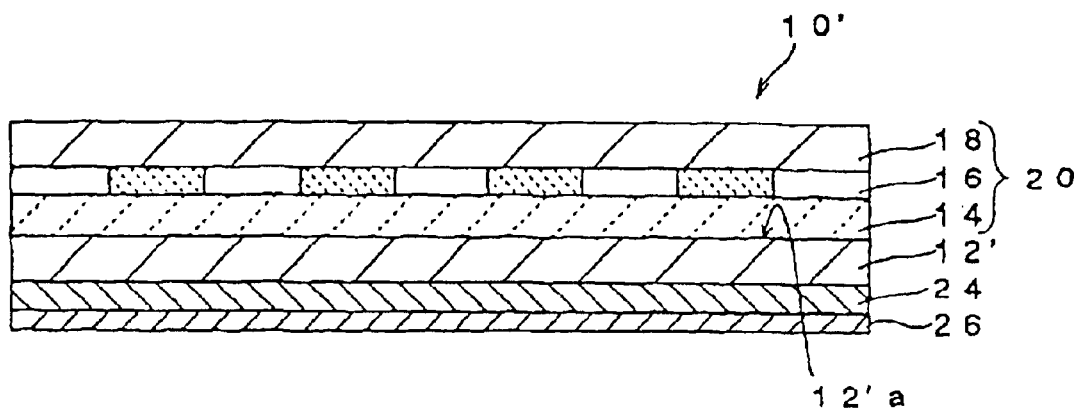
FIGS. 2A, 2B and 2C show schematic illustrations of a detecting label relating to another embodiment of the invention. Herein.
Figure 2B:
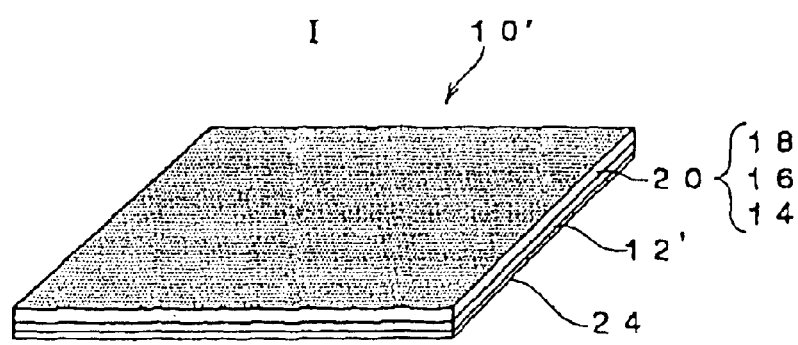
Figure 2C:
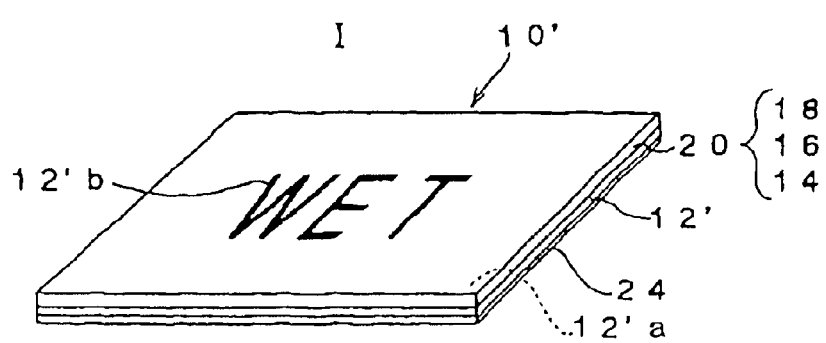

FIG. 2A shows a schematic sectional diagram of a detecting label relating to another mode for carrying out the invention, FIG. 2B shows an oblique view of the detecting label before contact with water, and FIG. 2C is an oblique view of the detecting label after contact with water. Additionally, the members that the detecting labels shown in FIGS. 1A, 1B and 1C and FIGS. 2A, 2B and 2C have in common are denoted individually by common reference numerals, and detailed descriptions thereof are omitted.

On the surface 12'a of the support 12' in the detecting label 10', letters and/or a pattern is printed in color of a similar hue to that of the colorant layer 18. Before the detecting label is brought into contact with water or moisture, as shown in FIG. 2B, the interlayer 16 keeps the decoloring agent layer 14 and the colorant layer 18 in a non-contact state, and so decoloring reaction does not proceed between the decoloring agent and the colorant. Accordingly, only the color of the colorant layer 18 is perceptible when viewed from outside I, and the letters and/or pattern on the support surface 12'a is not perceptible because their color is similar in hue to the colorant's color. When the detecting label 10' is exposed to water or moisture, as explained hereinbefore, the colorant held in the colorant layer 18 and/or the decoloring agent held in the decoloring agent layer 14 diffuses into the channels 22 and comes into contact with each other. As a result, the colorant layer 18 loses its color and, as shown in FIG. 2C, the letters 12'b printed on the surface 12'a of the support 12' are seen when viewed from outside I. By visual recognition of these letters 12'b, exposure of the detecting label 10'-affixed article to water or moisture can be detected.

Although the support surface 12'a of the support 12' is utilized as a display plane in this mode for performance, the display plane may be arranged inside the detecting layer (or the layer constituted of the decoloring agent layer 14, the interlayer 16 and the colorant layer 18). For instance, the display plane may be formed by printing letters and/or a pattern on the surface of the decoloring agent layer 14 or the interlayer 16 in hydrophobic ink.

It is preferable that the color of letters and/or a pattern drawn on the display plane be not only similar in hue to that of the colorant, but also brighter and lighter than the colorant's color. In drawing letters and/or a pattern, it is preferable to use highly waterproof or moisture-proof ink so as not to cause reduction in visual perception, e.g., bleeding, upon contact with a liquid to be detected. For an embodiment of detecting a history of contact with water or moisture, it is preferable to print letters or a pattern on the display plane in highly waterproof ink. The method for printing letters or a pattern on the display plane (e.g., the support surface) is not particularly restricted, but any of methods including inkjet printing, screen printing, lithographic printing, gravure printing, graphic arts using an electrophotographic process and SDB photography may be adopted.

In the mode of having a display plane, a light scattering layer may also be placed on the display plane for the purpose of avoiding visual recognition of letters or a pattern drawn on the display plane prior to disappearance of the detecting layer's color. And it is preferable for the light scattering layer to have a property that it becomes permeable to light upon contact with water or moisture. For instance, the light scattering layer can be a gelatin layer throughout which a great many air bubbles are dispersed. Since such a gelatin layer becomes permeable to light when the bubbles are destroyed by absorption of water or moisture, the light scattering layer comes to have light permeability simultaneously with disappearance of the detecting layer's color, permitting clear recognition of the display plane.

In a mode of forming no display plane, it is possible to detect contact with water or moisture by making letters or a pattern appear. For instance, channels are formed in a shape of letters and/or a pattern inside the interlayer of the detecting label 10, and thereby it becomes possible to expose the color of the support in the shape of the letters and/or the pattern against the background of the colorant layer's color. In the other way, the channels may be formed in a shape corresponding to the background of letters and/or a pattern. By doing so, it becomes possible to expose the color of the support surface as the background and display the letters and/or the pattern in the color of the colorant layer. Further, the decoloring agent layer of the detecting label 10 can be formed in a shape of letters and/or a pattern, and thereby the color of the colorant layer can be made to disappear in the shape of letters and/or pattern; as a result, the color of the support surface is exposed in the shape of letters and/or pattern against the background of the colorant layer's color.

On the other hand, it is also possible to form the decoloring agent layer in the shape corresponding to the background of letters and/or a pattern, and thereby display the letters and/or pattern in the color of the colorant layer against the background of the support surface's color.

In the foregoing modes for performance, white supports 12 and 12' are used. However, the color of the support is not particularly restricted so far as it enables clear recognition of color disappearance or the letters or pattern drawn on the display plane. Further, the support may be transparent. In this case, the color after decoloring reaction occurs or the background color of the letters or pattern on the display plane which becomes visible after decoloring reaction occurs is the color of an article to which the detecting label is affixed. Furthermore, the support may be resistant to water or permeable to moisture. Examples of a water-resistant support include synthetic paper (made from, e.g., polyolefin or polystyrene), plastic film (made from semi-synthetic or whole synthetic polymer, such as cellulose nitrate, cellulose acetate, cellulose acetate butyrate, polystyrene, polyvinyl chloride, polyethylene, polypropylene, polyethylene terephthalate, polycarbonate or polyamide), laminated paper (paper coated or laminated with a baryta layer or film of α-olefin polymer, such as polyethylene, polypropylene or ethylene-butene copolymer), metal-deposited plastic film, metal foil, metal foil-laminated plastic film, and paper impregnated with synthetic resin or emulsion. Preferable examples of a moisture-permeable support include uncoated paper, such as base paper, wood-free paper and medium-quality paper, and coated paper, such as art paper, coat paper, cast-coated paper.

In the foregoing modes for carrying out the invention, supports are used. However, the mode wherein no support needs using may be adopted in the invention.

For convenience in affixing the present detecting label to articles, it is preferable that the support have an adhesive layer on the back. Before the label is used, release paper is preferably pasted on the adhesive layer in a peelable condition for convenience of handling. Further, the convenience to users can be improved by writing an explanation of usage on the back of the release paper (on the side opposite to the release paper surface to which the adhesive layer is affixed). Adhesives which can be contained in the adhesive layer include the same ones as described as examples of an adhesive usable in the interlayer.

Before use (and/or during suspension of use after use over a period of time), a protective film for protecting the detecting layer from an external environment can be affixed to the surface of the detecting layer (e.g., the surface of the colorant layer or the decoloring agent layer), and the protective film may be peeled apart on the occasion when the label is used. On the other hand, when the colorant used has low resistance to light or the label is used in a condition that it is exposed to sunlight over a long period of time, the label may be used as a light-resistant protective layer remains laminated on the surface of the detecting layer.

On the surface, back and/or inside of the detecting layer, a layer for controlling the permeation of liquid or liquid vapor to be detected can be placed. By doing so, the detecting label can be made available for the use necessitating detection of contact with liquid drops alone but not requiring detection of the presence of liquid vapor.

In the foregoing modes for carrying out the invention, the detecting labels are structured so as to laminate the decoloring agent layer, the interlayer and the colorant layer in this order. Also, the same effects can be attained by structuring the label so that the colorant layer, the interlayer and the decoloring agent layer are arranged in order of mention. In the mode where the decoloring agent layer is laminated above the colorant layer, it is preferable to render the decoloring agent layer colorless and transparent, because the color change in the detecting layer can be clearly detected.

The sizes and shapes of detecting labels according to the foregoing modes have no particular limitations, but they can be determined depending on the desired purposes.

By properly designing and selecting the structures of the detecting labels 10 and 10' as mentioned above, the detecting levels of the detecting labels can be controlled according to their respective purposes, e.g., purposes of detecting wetness alone, exposure to the air having a moisture content beyond a certain limit and exposure to highly humid air over a period beyond a certain limit. Further, the detecting label can be designed so as to have two or more areas differing in detecting level, and thereby it becomes possible to provide an integral-unit mode of detecting label capable of indicating which humidity level (water wetting, or ultrahigh, high or medium humidity level) the label-affixed article is exposed to.

The present detecting material can be made using various methods. In the case of designing a detecting material as the label illustrated above, which is one mode for carrying out the invention, the material can be made utilizing various methods, such as a dry method, a wet method and a combination thereof. For instance, the detecting material can be made by forming a decoloring agent layer, an interlayer and a colorant layer (reversely, a colorant layer, an interlayer and a decoloring agent layer) on temporary supports individually, and then transferring those layers onto a support by sequential lamination technique. Each of those layers can be formed by coating on a temporary support a coating composition prepared by dispersing or dissolving ingredients in an appropriate solvent and then drying the composition coated. For forming each layer, the other way may be adopted, wherein ingredients for each layer are molten and extruded onto a temporary support. The interlayer having a plurality of channels or a pattern of letters can also be formed, as mentioned hereinbefore, using a printing technique (especially a silkscreen or gravure printing technique). The layers thus formed on temporary supports can be laminated successively on a support by the use of a hot melt, dry or wet lamination technique. In the case where the interlayer contains an adhesive, it is preferable to bond the interlayer to the decoloring agent layer and/or the colorant layer by the use of a hot melt lamination technique.

On the other hand, each layer may be formed directly on a support. For instance, after the decoloring agent layer or the colorant layer is formed on a support by the use of a hot melt extrusion or coating technique, the interlayer is formed on the decoloring agent or colorant layer by the use of a printing technique. In forming the colorant layer or the decoloring agent layer on the interlayer, it is preferable to adopt a dry method from the viewpoint of preventing the decoloring reaction from proceeding during the layer formation. More specifically, it is preferable that the colorant layer or the decoloring agent layer formed on a temporary support be transferred onto the interlayer by the use of a lamination technique. Therein, it is preferable to adopt a hot melt lamination technique when the interlayer contains an adhesive. Further, it is possible to form the decoloring agent layer or the colorant layer on a PET film capable of functioning as a protective film and subject it to the lamination processing as described above, thereby forming a detecting layer and, at the same time, laminating the protective film on the detecting layer.

As a mode for carrying out the invention, the detecting label for detection of water or moisture is illustrated above. However, the invention should not be construed as being limited to such a mode, but the present detecting material includes modes of detecting the liquids, the liquid vapors or both in which at least either the colorant or the decoloring agent is soluble in spite of the kinds of the liquid. In such modes, detecting materials can be constituted so as to detect liquids other than water by using colorants and decoloring agents in varying combinations and changing the kind of binder used together therewith. In addition, the detecting materials for detection of liquids other than water can also be made up by changing from the foregoing means for isolating the colorant from the decoloring agent to varying ones.

The present detecting materials can be preferably used for detecting moisture and/or wetness. For instance, the detecting materials can be affixed to articles having worry about deterioration from moisture, such as computers, precision instruments like communications apparatus, chemicals, various kinds of records, foods, clothes and cultural assets, and whether or not the articles have been brought into contact with moisture and/or water during the storage, transportation or use can be determined by visual inspection of the detecting materials. The detecting materials may be stuck directly on articles to be transported or stored, or affixed to package surfaces, such as cardboard box surfaces.

Further, the present detecting materials can be utilized in investigating and determining what caused failures of commodity products (whether or not commodity products have undergone exposure to water or high humidity in use). Furthermore, the present detecting materials can also utilized for determining whether or not the articles to come in contact with water in use, such as razor blades and water purification apparatus, have already been used. In addition, the present detecting materials affixed to indoor walls and windows can be used for ascertaining a distribution of humidity and formation of condensation inside a room.

Now, the invention will be illustrated below in more detail by reference to the following examples. It will be apparent to one skilled in the art that various changes and modifications can be made as to the materials, reagents, proportions and operations used in the examples without departing from the spirit and scope of the invention. Therefore, the invention should not be construed as being limited to the following examples.

EXAMPLE 1

<Support and Protective Sheet>

A polyethylene layer containing titanium dioxide surface-treated with aluminum oxide in a proportion of 18% by weight to the polyethylene was laminated on a paper support.

The laminated paper support was cut into equal halves, and one half of the paper support was subjected to corona discharge treatment and then coating of a gelatin subbing layer on one side, and further provided with a release paper-attached adhesive layer on the other side, thereby preparing a support. The other half of the laminated paper support was used as a protective sheet.

<Colorant Layer>

In 100 ml of water, 3 g of Dye 1 and 5 g of gelatin was mixed, and stirred for 30 minutes. Further, the stirring was continued for 30 minutes at 50° C. Then, 2 ml of formaldehyde (35%) was added to the dye-containing gelatin solution. The resulting solution was coated on the foregoing support by means of a bar coater so as to have a thickness of 3 $\mu$m, and then dried with 60–100° C. hot air.

<Isolation Layer (Display Layer)>

A commercially available double-faced adhesive tape was stamped into W-E-T letter combinations measuring about 5 mm in each stroke with a 2-cm spacing between combinations. The release paper on one side was peeled away, and the resulting tape was stuck on the colorant layer to form an isolation layer (display layer).

<Decoloring Agent Layer>

In 100 ml of water, 3 g of sodium sulfite and 5 g of gelatin was mixed, and stirred for 30 minutes. Further, the stirring was continued for 30 minutes at 50° C. Then, 2 ml of formaldehyde (35%) was added to the sodium sulfite-containing gelatin solution. The resulting solution was coated on the foregoing protective sheet by means of a bar coater so as to have a thickness of 5 $\mu$m, and then dried with 60–100° C. hot air.

<Production of Detecting Sheet>

The release paper of the isolation layer was peeled away, and on the resulting isolation layer was stuck the decoloring agent layer to produce a detecting sheet A-1.

EXAMPLE 2

A detecting sheet B-1 was produced in the same manner as in Example 1, except that the places were changed between the colorant layer and the decoloring agent layer.

EXAMPLE 3

Detecting sheets A-2 to A-8 and detecting sheets B-2 to B-8 were produced in the same manner as in Example 1 and Example 2 respectively, except that the Dye 1 was replaced by the dyes shown in Table 1.

Comparative Example 1

A detecting sheet C was prepared in the same manner as in Example 1, except that sodium sulfite was not added at all in forming the decoloring agent layer.

[Evaluation]

After peeling the protective sheet off each of the detecting sheets A-1 to A-8, B-1 to B-8 and C-1, each of the resulting sheets (referred to as "detecting sheet" hereinafter) was allowed to stand under the following conditions a, b and c each. After testing, the mark "WET" in each detecting sheet was observed, and thereby the moisture sensing ability was checked. The results obtained are shown in Table 1.

a. Letting each detecting sheet stand for one hour at 50° C. under the humidity of 98%.
b. Letting each detecting sheet stand for 3 days at 25° C. under the humidity of 40%.
c. Immersing each detecting sheet in water for 1 second.

TABLE 1

| Detecting sheet | Dye | a | b | c |
| --- | --- | --- | --- | --- |
| A-1 | 1 | ○ | ● | ○ |
| A-2 | 5 | ○ | ● | ○ |
| A-3 | 12 | ○ | ● | ○ |
| A-4 | 15 | ○ | ● | ○ |
| A-5 | 18 | ○ | ● | ○ |
| A-6 | 34 | ○ | ● | ○ |
| A-7 | 38 | ○ | ● | ○ |
| A-8 | 46 | ○ | ● | ○ |
| B-1 | 1 | ○ | ● | ○ |
| B-2 | 5 | ○ | ● | ○ |
| B-3 | 12 | ○ | ● | ○ |
| B-4 | 15 | ○ | ● | ○ |

TABLE 1-continued

| Detecting sheet | Dye | a | b | c |
|---|---|---|---|---|
| B-5 | 18 | ○ | ● | ○ |
| B-6 | 34 | ○ | ● | ○ |
| B-7 | 38 | ○ | ● | ○ |
| B-8 | 46 | ○ | ● | ○ |
| C | 1 | ● | ● | ● |

○: Color disappears and the mark "WET" is readable.
●: Color does not disappear and the mark "WET" is illegible.

On the other hand, the detecting sheets keeping protective sheets on were each allowed to stand under the same conditions as mentioned above, and the protective sheets were peeled away therefrom at the time of observation. Disappearance of color in the shape of WET was not observed in any of the detecting sheets.

As can be seen from the testing results shown above, the present detecting sheets were highly responsive to high humidity and wetting with water and thereby the mark "WET" were clearly readable, and besides, their colors were not lost by storage under ordinary condition. Further, they were stable under the condition that they were covered with protective sheets. In other words, their shelf lives were long.

EXAMPLE 4

A detecting label having the same structure as the detecting label 10' shown in FIGS. 2A, 2B and 2C was produced in the following process, except that the display plane was not support surface 12'a but the support back (the side being in contact with the adhesive layer 24. In addition, a protective film was arranged on the colorant layer 18.

An aqueous gelatin solution containing sodium sulfite (decoloring agent) and formaldehyde was coated on a 75 μm-thick transparent PET film (support) to prepare a film (1). Therein, the ratio of the gelatin to the sodium sulfite was 2:1 by weight, and the coating thickness was 5 μm on a dry basis.

An aqueous gelatin solution containing Dye 1 (colorant) and formaldehyde was coated on a 25 μm-thick transparent PET protective film to prepare a film (2). Therein, the ratio of the gelatin to the dye was 10:1 by weight, and the coating thickness was 5 μm on a dry basis. Then, the gelatin side of the film (1) was brought into contact with the gelatin side of the film (2), and they were bonded to each other by the use of a hot melt adhesive. In this bonding step, adhesive-free spaces as channels were formed in the layer comprising the foregoing adhesive (interlayer). The thickness of this interlayer was about 25 μm. On the PET film of the film (1) and the side opposite to the gelatin layer side, letters were printed in UV curable ink, and then a hot melt adhesive was coated to form an adhesive layer. To this adhesive layer, a release paper was affixed.

In the thus produced detecting label, disappearance of color was caused under a relative humidity of 80% or higher at both of the temperatures 23° C. and 40° C. It was confirmed by this experiment that this detecting label enabled detection of moisture.

In accordance with the invention, the colored composition loses its color irreversibly upon contact with moisture or water, and both colored state before undergoing testing conditions and color-lost state after testing are stable. Therefore, clear and reliable detection of moisture or wetness can be effected by the invention. By the detecting material being cut off from moisture under a condition that the color density is lowered to a certain extent in testing, it becomes possible to know a history as the product of humidity and time from such a color density. When this method is adopted, the present detecting label enables the easy and reliable detection of a history of exposure to moisture/wetness only by being affixed to an article to be examined and the package surface thereof. Further, with respect to the articles having a detecting function according to the present method or detecting label, the history of transportation after shipment of products and the history of storage can be checked easily, so the invention is advantageous for this usage also. Furthermore, the invention can provide a detecting material by which the history of contact with a liquid, such as water, or a liquid vapor can be easily detected by change in color, and a detection method by which contact of various articles with a liquid, such as water, or a liquid vapor during the use, storage or transportation can be determined with ease.

While the invention has been described in detail and with reference to specific embodiments thereof, it will be apparent to one skilled in the art that various changes and modifications can be made therein without departing from the spirit and scope thereof.

What is claimed is:

1. A method of detecting moisture or wetness comprising:
   (i) placing a composite material, which contains at least one water-soluble decoloring agent and at least one methine dye, on an article that may be exposed to moisture or wetness wherein the dye and decoloring agent are initially spatially isolated from each other on the article and upon exposure to moisture or wetness the dye and/or the decoloring agent migrate towards each other on the article to react and decolor the dye;
   (ii) exposing the article to moisture or wetness; and
   (iii) observing a disappearance of color from the composite material indicating exposure to moisture or wetness.

2. A label for detecting moisture or wetness, comprising a support coated with at least one water-soluble decoloring agent and at least one methine dye, wherein the dye and decoloring agent are initially spatially isolated from each other on the support and upon exposure to moisture or wetness the dye and/or the decoloring agent migrate towards each other on the support to react and decolor the dye.

3. An article having a moisture/wetness detecting function, which is fitted with a moisture- or water-detecting component comprising a support coated with at least one water-soluble decoloring agent and at least one methine dye wherein the dye and decoloring agent are initially spatially isolated from each other on the support and upon exposure to moisture or wetness the dye and/or the decoloring agent migrate towards each other on the support to react and decolor the dye.

4. A material for detection of contact with a liquid, a liquid vapor or both, comprising on a support at least one decoloring agent and at least one colorant wherein the colorant and decoloring agent are initially spatially isolated from each other on the support and upon exposure to liquid, the liquid vapor or both, the colorant and/or the decoloring agent migrate towards each other on the support to react and decolor the colorant.

5. The detecting material according to claim 4, wherein the colorant is a methine dye or an azomethine dye.

6. The detecting material according to claim 4, comprising a detecting layer comprising at least one layer comprising the decoloring agent and the colorant in a state that the decoloring agent and the colorant are spatially isolated from each other, wherein at least a part of the detecting layer loses or changes its color upon contact with a liquid, a liquid vapor or both in which at least either the decoloring agent or the colorant is soluble.

7. The detecting material according to claim 6, further comprising underneath or inside the detecting layer a display plane bearing characters, drawings or both, and enabling the characters, drawings or both to get visual recognition when a part or all of the detecting layer loses its color.

8. The detecting material according to claim 6, wherein the detecting layer comprises a decoloring agent layer containing the decoloring agent and a colorant layer containing the colorant.

9. The detecting material according to claim 8, further comprising a member for leaving a space between the decoloring agent layer and the colorant layer in a state that the liquid, the liquid vapor or both is capable of permeating through the member.

10. The detecting material according to claim 8, further comprising an interlayer that is sandwiched between the decoloring agent layer and the colorant layer and has channels leading to both the decoloring agent layer and the colorant layer.

11. The detecting material according to claim 10, wherein the interlayer has a thickness of 0.1 to 100 $\mu$m.

12. The detecting material according to claim 8, wherein both decoloring agent layer and colorant layer further comprise a binder capable of absorbing the liquid, the liquid vapor or both.

13. The detecting material according to claim 12, wherein the liquid is water and the binder is gelatin.

14. A method of detecting moisture or wetness comprising:

(i) placing a composite material, which contains at least one water-soluble decoloring agent and at least one methine dye, on an article that may be exposed to moisture or wetness wherein the dye and decoloring agent are initially spatially isolated from each other on the composite material and upon exposure to moisture or wetness the dye and/or the decoloring agent migrate towards each other on the composite material to react and decolor the dye;

(ii) exposing the article to moisture or wetness;

(iii) migration of the dye and/or the decoloring agent towards each other on the composite material; and (iv) observing a disappearance of color from the composite material indicating exposure to moisture or wetness.

* * * * *